United States Patent
Chenault

(10) Patent No.: US 10,365,210 B2
(45) Date of Patent: *Jul. 30, 2019

(54) POLARIMETRIC DETECTION OF FOREIGN FLUIDS ON SURFACES

(71) Applicant: Polaris Sensor Technologies, Inc., Huntsville, AL (US)

(72) Inventor: David B. Chenault, Huntsville, AL (US)

(73) Assignee: Polaris Sensor Technologies, Inc., Huntsville, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/975,958

(22) Filed: May 10, 2018

(65) Prior Publication Data

US 2018/0328836 A1 Nov. 15, 2018

Related U.S. Application Data

(63) Continuation of application No. 15/387,901, filed on Dec. 22, 2016, now Pat. No. 9,970,861, which is a
(Continued)

(51) Int. Cl.
*G01N 21/21* (2006.01)
*G01N 33/18* (2006.01)
(Continued)

(52) U.S. Cl.
CPC .............. *G01N 21/21* (2013.01); *G01N 25/00* (2013.01); *G01N 33/1833* (2013.01);
(Continued)

(58) Field of Classification Search
CPC ........... G01N 21/21; G01N 2021/1793; G01N 2021/4792; G01N 21/3581; G01N 2201/0683; G01N 25/00; G01N 33/1833; G06K 9/0063; G06K 9/2036; G06T 5/50; G06T 2207/10048; G06T 2207/30181
(Continued)

(56) References Cited

U.S. PATENT DOCUMENTS 3,783,284 A * 1/1974 McCormack ........ G01N 21/314
250/301
7,009,550 B2 * 3/2006 Moeller-Jensen ..........................
G01N 33/1833
342/26 C
(Continued)

*Primary Examiner* — Taeho Jo
(74) *Attorney, Agent, or Firm* — Angela Holt; Bradley Arant Boult Cummings LLP

(57) ABSTRACT

A method for detecting the presence of foreign fluids on surface comprises estimating an expected polarization response for a foreign fluid desired to be detected. Oil from an oil spill is one such foreign fluid. A polarimeter records raw image data of a surface (e.g., the surface of water) to obtain polarized images of the surface. IR and polarization data products are computed from the polarized images. The IR and polarization data products are converted to multi-dimensional data set to form multi-dimensional imagery. Contrast algorithms are applied to the multi-dimensional imagery to form enhanced contrast images, from which foreign fluids can be automatically detected.

14 Claims, 11 Drawing Sheets
(2 of 11 Drawing Sheet(s) Filed in Color)

Related U.S. Application Data continuation of application No. 14/843,835, filed on Sep. 2, 2015, now Pat. No. 9,528,929.

(60) Provisional application No. 62/044,682, filed on Sep. 2, 2014.

(51) Int. Cl.
| | | |
|---|---|---|
| *G01N 25/00* | (2006.01) | |
| *G06T 5/50* | (2006.01) | |
| *G06K 9/20* | (2006.01) | |
| *G06K 9/00* | (2006.01) | |
| *G01N 21/17* | (2006.01) | |

(52) U.S. Cl.
CPC ......... *G06K 9/0063* (2013.01); *G06K 9/2036* (2013.01); *G06T 5/50* (2013.01); *G01N 2021/1793* (2013.01); *G06T 2207/10048* (2013.01); *G06T 2207/30181* (2013.01)

(58) Field of Classification Search
USPC ..................................................... 250/338.1
See application file for complete search history.

(56) References Cited

U.S. PATENT DOCUMENTS

| | | | | |
|---|---|---|---|---|
| 7,688,428 B2* | 3/2010 | Pearlman | .................. | G01J 3/02 356/70 |
| 8,124,931 B2* | 2/2012 | Andrews | ................ | G01N 21/35 250/301 |
| 8,217,368 B2* | 7/2012 | Meyers | .................. | G01N 21/21 250/459.1 |
| 2001/0048078 A1* | 12/2001 | Stair | ..................... | G01N 21/21 250/340 |
| 2004/0036855 A1* | 2/2004 | Hammer | ................ | G01N 21/21 356/70 |
| 2004/0257264 A1* | 12/2004 | Moeller-Jensen | .......................... | G01N 33/1833 342/52 |
| 2008/0165359 A1* | 7/2008 | Mattox | ..................... | G01J 4/04 356/367 |
| 2009/0039255 A1* | 2/2009 | Andrews | ................. | G01N 21/35 250/301 |
| 2010/0096554 A1* | 4/2010 | Shirota | ................... | G01N 21/94 250/341.8 |
| 2012/0089332 A1* | 4/2012 | Hong | ...................... | G01S 13/88 702/2 |
| 2012/0112096 A1* | 5/2012 | Meyers | .................. | G01N 21/21 250/459.1 |
| 2012/0183175 A1* | 7/2012 | Alouini | ................... | G01J 3/447 382/103 |
| 2013/0320216 A1* | 12/2013 | Aiko | ..................... | G01B 11/303 250/349 |
| 2014/0159937 A1* | 6/2014 | Beadle | .................... | G01S 7/025 342/22 |
| 2014/0159938 A1* | 6/2014 | Shipley | .................... | G01V 3/12 342/22 |
| 2015/0168210 A1* | 6/2015 | Dorschner | ............ | G01J 1/0429 349/18 |
| 2016/0003677 A1* | 1/2016 | Pezzaniti | .................. | G01J 5/58 250/330 |

\* cited by examiner

US 10,365,210 B2

POLARIMETRIC DETECTION OF FOREIGN FLUIDS ON SURFACES

REFERENCE TO RELATED APPLICATIONS

This application is a continuation of and claims priority to U.S. Non-Provisional patent application Ser. No. 15/387,901, entitled "Wide-Area Real-time Method for Detecting Foreign Fluids on Water Surfaces," and filed on Dec. 22, 2016, which is a continuation of U.S. Non-Provisional patent application Ser. No. 14/843,835, filed on Sep. 2, 2015, and issued as U.S. Pat. No. 9,528,929, which claims priority to U.S. Provisional Patent Application Ser. No. 62/044,682, entitled "Polarimetry for the Detection of Oil on Water" and filed on Sep. 2, 2014. All of the prior applications are fully incorporated herein by reference.

GOVERNMENT LICENSE RIGHTS

This invention was made with government support under Contract Number W31P4Q-09-C-0644 awarded by the U.S. Army. The government has certain rights in the invention.

BACKGROUND AND SUMMARY

As used herein, Long Wave Infrared is referred to as "LWIR" or "thermal." As used herein, Mid Wave Infrared is referred to as "MWIR." As used herein, Short Wave Infrared is referred to as "SWIR." As used herein, Infrared is referred to as "IR." As used herein, Infrared refers to one, a combination, or all of these subsets of the Infrared spectrum.

A method using Infrared Imaging Polarimetry for the detection of foreign fluids on water surfaces is disclosed herein. The described method is not tied to any one specific polarimeter sensor architecture and thus the method described pertains to all Infrared sensors capable of detecting the critical polarimetric signature. The described method is not tied to any one specific portion or subset of the Infrared spectrum and thus the method described pertains to all sensors that operate in one or more of the LWIR, MWIR, or SWIR. The method comprises modeling of the foreign fluid on water or measurements of the foreign fluid on water under controlled conditions to understand the polarization response. This is done in order to select the best angles over which the detection will be most effective. The polarimeter is then mounted on a platform such that the sensor points towards the surface within the range of the acceptable angles. The polarimeter is then used to record raw image data of an area using a polarimeter to obtain polarized images of the area. The images are then corrected for non-uniformity, optical distortion, and registration in accordance with the procedure necessitated by the sensor's architecture. IR and polarization data products are computed, and the resultant data products are converted to a multi-dimensional data set for exploitation. Contrast enhancement algorithms are applied to the multi-dimensional imagery to form enhanced images. The enhanced images may then be displayed to a user, and/or an annunciator may announce the presence of the foreign fluid on the surface of the water.

DESCRIPTION OF THE DRAWINGS

The patent or application file contains at least one drawing executed in color. Copies of this patent or patent application publication with color drawings will be provided by the Office upon request and payment of the necessary fee.

FIG. 11c is an exemplary thermal image of the foreign fluid FIG. 11a on water at night, with the polarimeter at a shallower angle than the image of FIG. 11a.

FIG. 12b is a polarization image of the foreign fluid on water of FIG. 12a.

FIG. 12c is a ColorFuse image of the foreign fluid on water of FIG. 12a.

FIG. 13b is a visible image of the spill of FIG. 13a.

DETAILED DESCRIPTION

Figure 1:
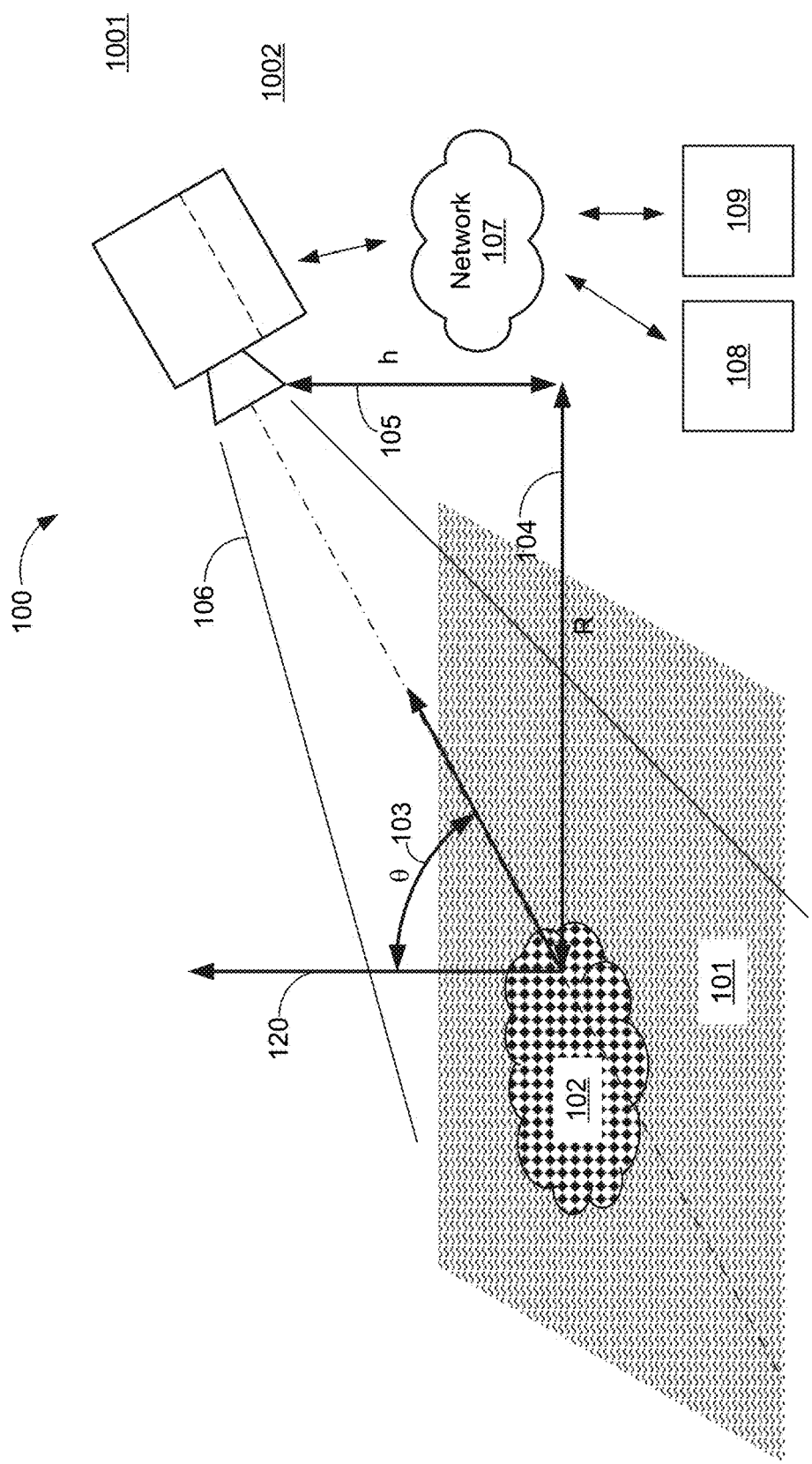
FIG. 1 is a diagram illustrating a system in accordance with an exemplary embodiment of the present disclosure.

FIG. 1 illustrates a polarimeter system 100 in accordance with an exemplary embodiment of the present disclosure. The system 100 comprises a polarimeter 1001 and a signal processing unit 1002, which collect and analyze images of a water surface 101 for detection and annunciation of the presence of a foreign fluid 102 on the water surface. An exemplary foreign fluid 102 shown in FIG. 1 is petroleum from natural seepage, a leak from an oil drilling or processing facility, or a leak from a vessel, or from a vessel that was intentionally dumped overboard. As used in this disclosure, the terms "oil" or "foreign fluid" may refer to any liquid that is desired to be detected.

The polarimeter system 100 comprises a polarimeter 1001 for recording polarized images, such as a digital camera or IR imager that collects images. The polarimeter 1001 may be mounted on a tower or platform (not shown) such that it views the water surface 101 at an angle θ 103 from a normal direction 120 to the water surface 101 and at a horizontal range "R" 104 from a general center of the field of view to the polarimeter 1001, and a height "h" 105 defined by the vertical distance from the water surface 101 to the polarimeter 1001. The area imaged by the polarimeter is depicted by a field of view 106.

The polarimeter 1001 transmits raw image data to the signal processing unit 1002, which processes the data as further discussed herein. The processed data is then displayed to an operator (not shown) via a display 108. Alternatively, detection is annunciated on an annunciator 109, as further discussed herein. Although FIG. 1 shows the polarimeter 1001 and the signal processing unit 1002 as a combined unit, in certain embodiments the polarimeter 1001 and signal processing unit 1002 are separate units. For example, the polarimeter 1001 may be mounted remotely on a platform or tower (not shown) and the signal processing unit 1002 placed close to the operator. Similarly, the display 108 or annunciator 109 can be packaged with the system 100 or packaged with the signal processing unit 1002 or be separate from all other components and each other.

In the illustrated embodiment, the polarimeter 1001 sends raw image data (not shown) to the signal processing unit 1002 over a network or communication channel 107 and processed data sent to the display 108 and annunciator 109. The signal processing unit 1002 may be any suitable computer known in the art or future-developed. The signal processing unit 1002 receives the raw image data, filters the data, and analyzes the data as discussed further herein to provide enhanced imagery and detections and annunciations. The network 107 may be of any type network or networks known in the art or future-developed, such as a simple communications cable, the internet backbone, Ethernet, Wifi, WiMax, wireless communications, broadband over power line, coaxial cable, and the like. The network 107 may be any combination of hardware, software, or both. Further, the network 107 could be resident in a sensor (not shown) housing both the polarimeter 101 and the signal processing unit 107.

In the illustrated embodiment, the signal processing unit sends processed image data (not shown) to the display and annunciator over a network or communication channel 107 and processed data sent to the display 108 and annunciator 109.

Figure 2:
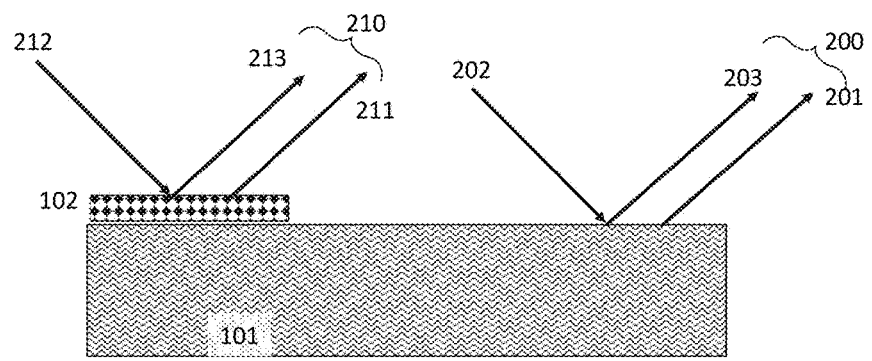
FIG. 2 shows an exemplary cross-section of reflected and emitted radiation from a prior art system in which an IR camera measures IR contrast between oil and water.

FIG. 2 shows an exemplary cross-section of reflected and emitted radiation from a prior art system in which an IR camera (not shown, with no polarization capability) measures IR contrast (i.e. radiance differences) between oil and water. In this embodiment, foreign fluid 102 is floating on a water surface 101. The radiation from the water surface 101 incident on an infrared camera viewing this scene senses a "summed" radiance 200 that is the sum of emitted radiation 201 from the water surface 101 and the reflected radiation 203 from the background 202 reflected off the surface 101. Likewise for the foreign fluid 102, the "summed" radiance 210 is the sum of the emitted radiation 211 from the foreign fluid 102 and reflected radiation 213 from the background 212 reflected off the foreign fluid 102.

The emitted radiation 201 depends on the temperature of the water 101 and the optical constant of the water, also known as the refractive index. The reflected radiation component 203 depends on the temperature of the background 202 and the optical constant of the water. Thus the summed radiance 200 depends on background temperature, water temperature, and water optical constants.

The emitted radiation 211 depends on the temperature of the foreign fluid 102 and the optical constant of the foreign fluid 102. The reflected radiation component 213 depends on the temperature of the background 212 and the optical constant of the foreign fluid 102. Thus the summed radiance 210 depends on the temperature of the foreign fluid 102, the optical constant of the foreign fluid, and the temperature of the background 212.

For detection of the foreign fluid using an IR camera, the summed radiances 200 and 210 must be different to result in radiance contrast. There are multiple possible combinations of the background and foreign fluid and water temperature values and variations in the foreign fluid optical constants such that there is very little difference in the summed radiances 200 and 210 resulting in low contrast and difficult detection of the foreign fluid.

Figure 3:
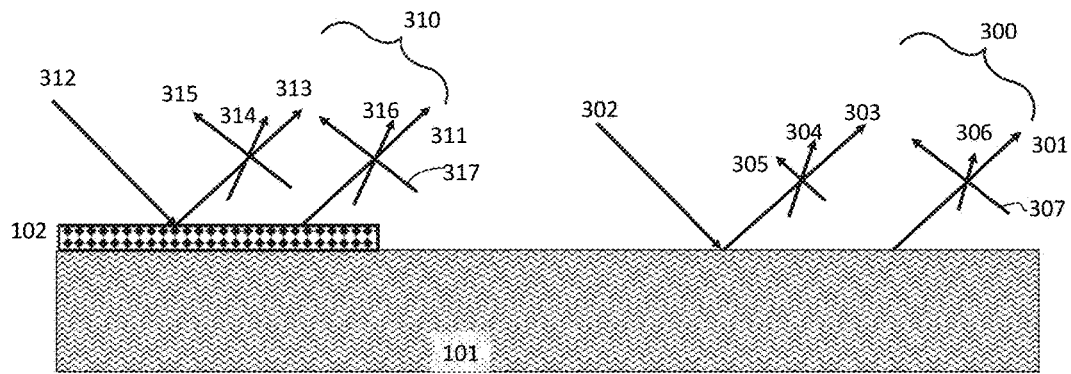
FIG. 3 is a representation of reflected and emitted radiation from an exemplary cross-section of one embodiment of the current invention in which a polarimeter measures IR contrast and polarization contrast between oil and water.

FIG. 3 is a representation of reflected and emitted radiation from an exemplary cross-section of one embodiment of the current invention in which a polarimeter (not shown) measures radiance contrast and polarization contrast between oil and water. In this embodiment, foreign fluid 102 is floating on a water surface 101. The summed radiation 300 from the water surface 101 is the sum of the emitted radiation 301 and the reflected radiation 303 from the background 302 reflected off the surface 101. As known by persons with skill in in the relevant art, the emitted radiation 301 consists of two polarization components, a "perpendicular" polarization component 306 and a "parallel" polarization component 307. The difference in these polarization components 306 and 307 results in a net polarization for the thermal emitted radiation 301.

Likewise, the reflected component 303 consists of two polarization components, a "perpendicular" polarization component 304 and a "parallel" polarization component 305, resulting from the reflection of the background radiation 302. The difference in these polarization components 304 and 305 results in a net polarization for the thermal emitted radiation 303. The total polarization signal from the water is a combination of the polarization signals from the emitted radiation 301 and reflected radiation 303. The net polarization signal is called the Degree of Linear Polarization or "DoLP".

Similarly, the summed radiation 310 from the foreign fluid surface 102 is the sum of the emitted radiation 311 and the radiation 313 from the background 312 reflected off the surface 102. The emitted radiation 311 consists of two polarization components, the "perpendicular" polarization component 316 and the "parallel" polarization component 317. The difference in these polarization components 316 and 317 results in a net polarization for the thermal emitted radiation 311. Likewise, the reflected component 313 consists of two polarization components, the "perpendicular" polarization component 314 and the "parallel" polarization component 315, resulting from the reflection of the background radiation 312. The difference in these polarization components 313 and 314 results in a net polarization signal for the thermal emitted radiation 313. The total polarization signal from the foreign fluid is a combination of the polarizations of 311 and 313. The detection of the foreign fluid occurs when the polarization contrast of the foreign fluid is different from the polarization contrast of the water.

Figure 4:
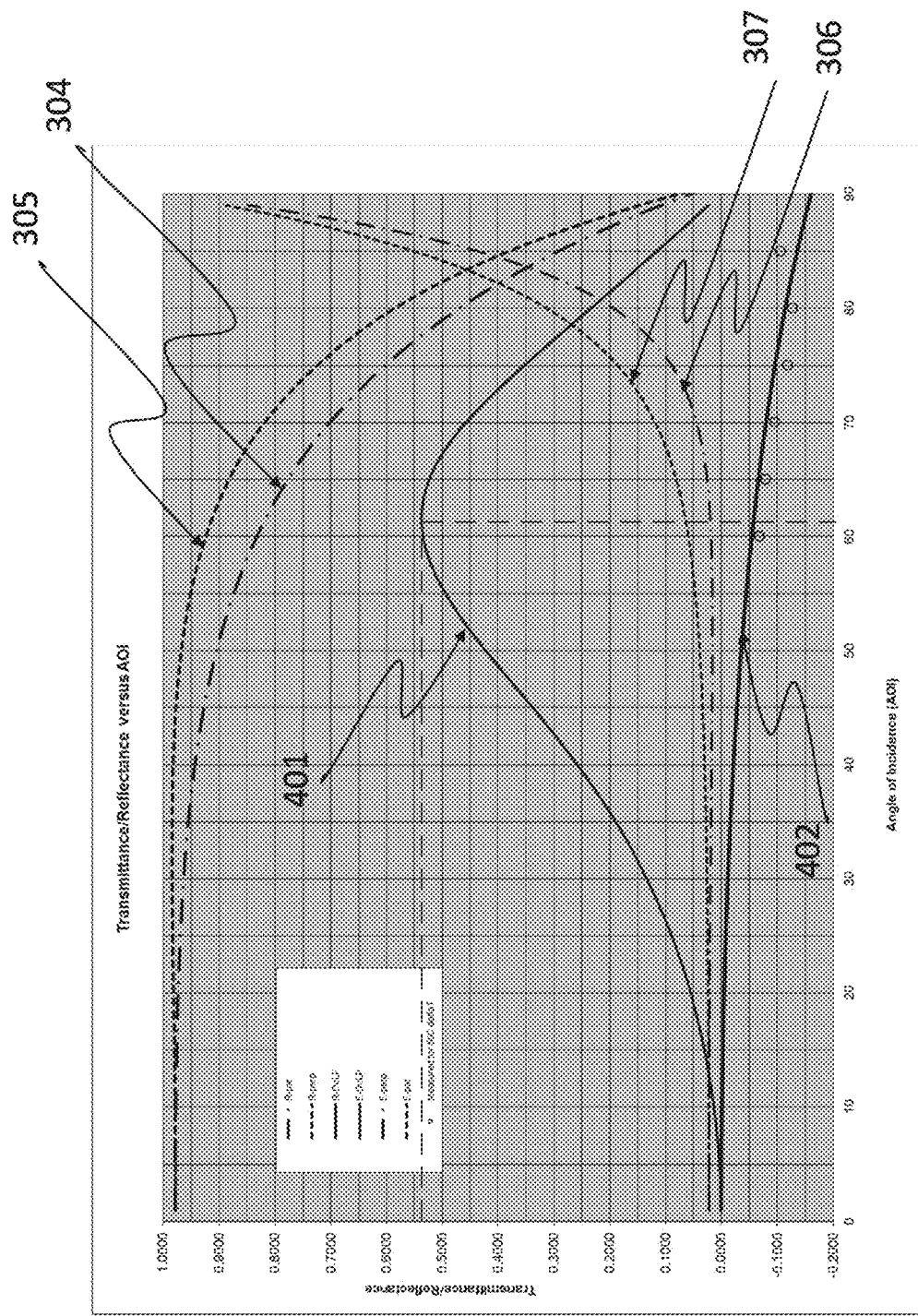
FIG. 4 depicts a model of the dependence of the polarization signals of water as a function of the angle of incidence.

FIG. 4 depicts a model of the dependence of the polarization signals of water as a function of the angle of incidence 103 (FIG. 1) and shows the perpendicular and parallel polarization components 304 and 305 for the reflected radiation and the perpendicular and parallel polarization components 306 and 307 of the emitted polarization. The DoLP results from the difference of perpendicular and parallel polarization components. The reflected DoLP 401 for the reflected radiation increases with increasing angle until it reaches a maximum of about 53% at an angle of about 62°. The emitted DoLP 402 for the emitted radiation monotonically decreases as a function of angle of incidence 103.

Figure 7:
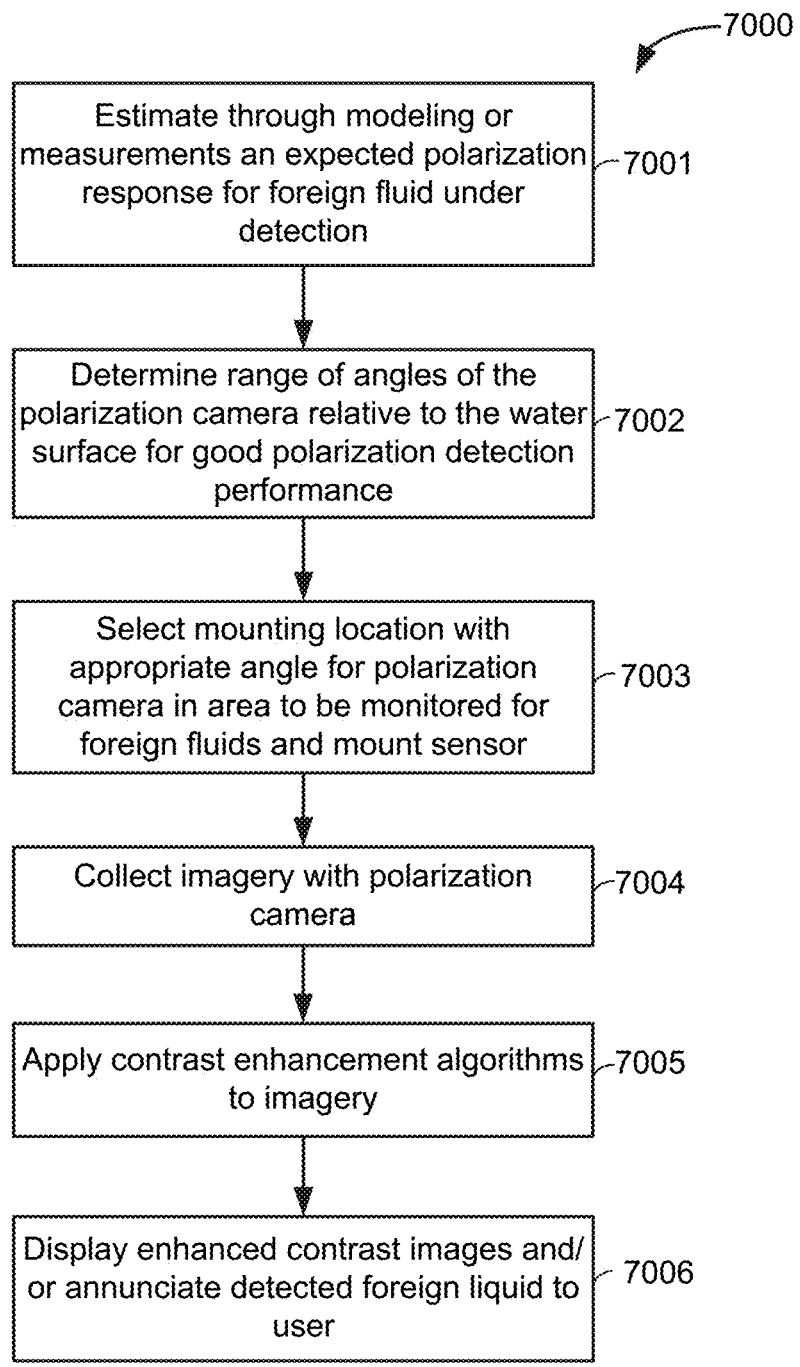
FIG. 7 depicts a block diagram of a method for detecting a foreign fluid on a water surface.

It is important to note that the shape and nature of these curves depends on the optical constants of the material and thus these curves are significantly different for the foreign liquid being detected. The differences in DoLP between water and the foreign liquid are exploited by the current invention. A higher contrast difference for detecting oil on water is attained by examining these curves for the polarization performance as a function of angle. In one embodiment of the current invention, the optimal angles based upon experimental data obtained with oil are between 70° and 88° from normal (angle θ 103) or between 2° and 20° elevation (measured from a horizontal). FIG. 7 is a block diagram of the process steps to achieve optimal detection that exploits these concepts.

Figure 5:
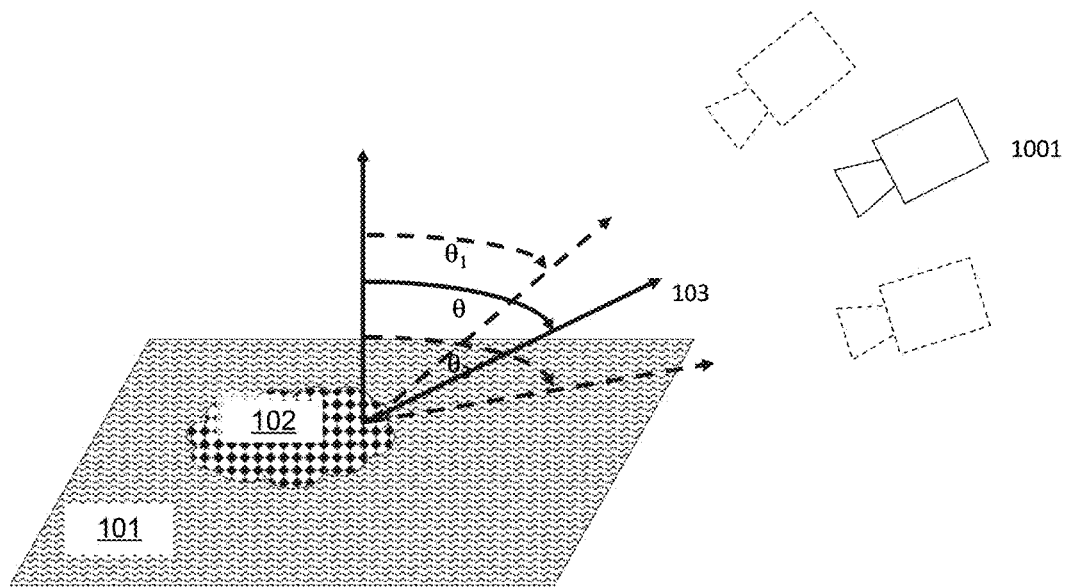
FIG. 5 depicts an exemplary positioning of the polarimeter to optimize the detection of a foreign fluid.

FIG. 5 depicts an exemplary positioning of the polarimeter 1001 to optimize the detection where the polarimeter 1001 is positioned between angles $\theta_1$ and $\theta_2$. Using the optimal range from FIG. 4 as an example, $\theta_1$ may be 70° and $\theta_2$ may be 88°, and the polarimeter placed within this range. For one embodiment of the invention in which the sensor is mounted on a tower (not shown), these angles can be achieved by selecting the appropriate Range R 104 (FIG. 1) and Height h 105 (FIG. 1).

Figure 6:
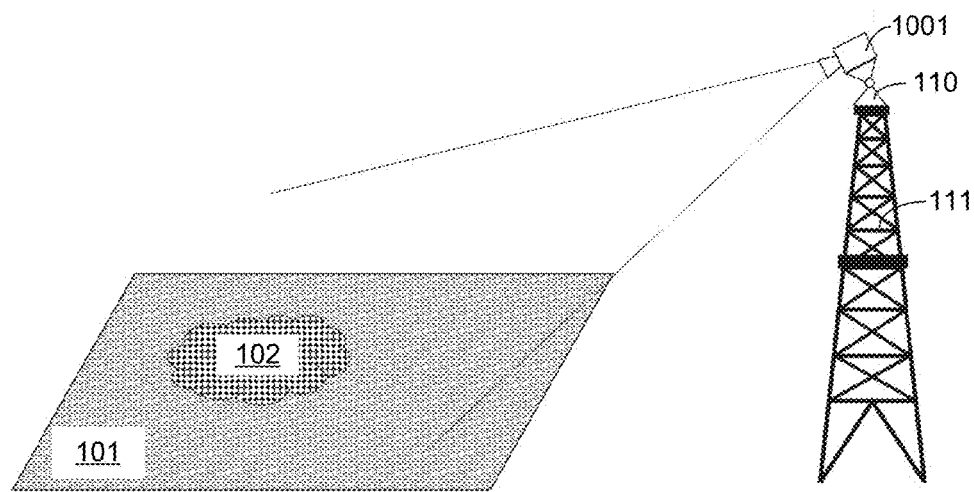
FIG. 6 depicts exemplary mounting of the polarimeter on a pan-tilt unit which is mounted on a tower on land.

FIG. 6 depicts exemplary mounting of the polarimeter on a pan-tilt unit 110 which is mounted on a tower 111 on land. In another exemplary embodiment, the tower 111 is a mast or pole. In another exemplary embodiment, the tower 111 is a platform or other mounting point on a structure overlooking the water surface to be monitored. In other embodiments, the tower, mast, pole, platform or mounting point can be placed on a vessel, floating platform, fixed pier or platform, floating buoy, or the like. In another exemplary embodiment, the sensor system 100 and pan-tilt unit 110 is placed on a manned or unmanned aerial vehicle. The sensor system further in some embodiments is portable and can be hand-held.

FIG. 7 depicts a block diagram of a method 7000 to detect a foreign fluid 102 (FIG. 1) on a water surface 101 (FIG. 1) in the optimal conditions. In step 7001, the polarized response of the foreign fluid is predicted through analysis of the emitted and reflected radiation of the fluid of interest, in the manner discussed with respect to FIGS. 3 and 4 herein. Alternatively, measurements of the fluid of interest can be performed experientially, or experimentally in a controlled environment such as a laboratory where the angles can be varied.

In step 7002 of the method 7000, the results of step 7001 are used to determine the range of angles $\theta_1$ and $\theta_2$ (FIG. 5) for good performance, as discussed with respect to FIGS. 4 and 5 herein. In step 7003, the results of step 7002 are used to determine the best mounting location for the mounting options available, range R 104 (FIG. 1) and height h 105 (FIG. 1), and the polarimeter 1001 (FIG. 1) is mounted.

In step 7004, imagery is collected with the polarimeter 1001 as is described herein. In step 7005, contrast enhancement algorithms are applied to the imagery to aid the detection of the foreign fluid by an operator or by autonomous detection algorithms. In step 7006, the enhanced contrast images are displayed and/or the detection of the foreign liquid is annunciated.

Figure 8:
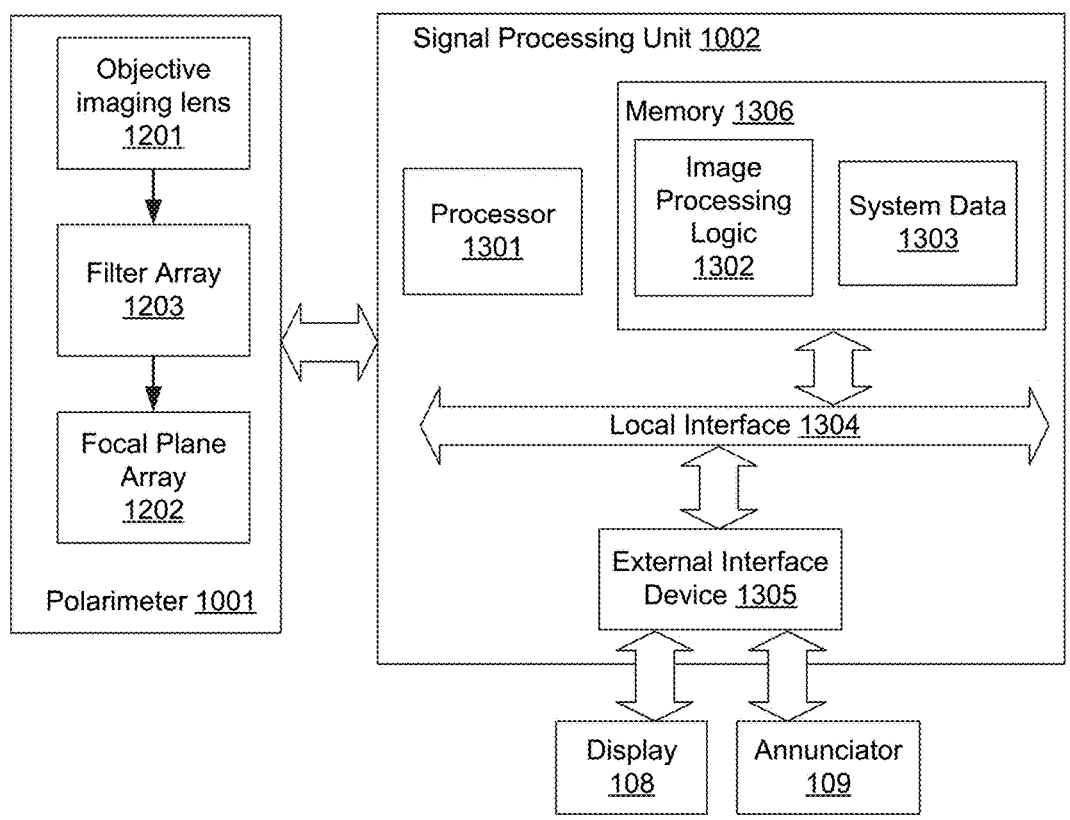
FIG. 8 depicts an exemplary polarimeter system comprised of a polarimeter and signal processing unit according to an embodiment of the present disclosure.

FIG. 8 depicts an exemplary polarimeter system 100 comprised of a polarimeter 1001 and signal processing unit 1002 according to an embodiment of the present disclosure. The polarimeter 1001 comprises an objective imaging lens 1201, a filter array 1203, and a focal plane array 1202. The objective imaging lens 1201 comprises a lens pointed at the water and foreign fluid surface 101 and 102 (FIG. 1). The filter array 1203 filters the images received from the objective imaging lens system 1201. The focal plane array 1202 comprises an array of light sensing pixels.

The signal processing unit 1002 comprises image processing logic 1302 and system data 1303. In the exemplary signal processing unit 1002 image processing logic 1302 and system data 1303 are shown as stored in memory 1306. The image processing logic 1302 and system data 1303 may be implemented in hardware, software, or a combination of hardware and software.

The signal processing unit 1002 also comprises a processor 1301, which comprises a digital processor or other type of circuitry configured to run the image processing logic 1302 by processing the image processing logic 1302, as applicable. The processor 1301 communicates to and drives the other elements within the signal processing unit 1002 via a local interface 1304, which can include one or more buses. When stored in memory 1306, the image processing logic 1302 and the system data 1303 can be stored and transported on any computer-readable medium for use by or in connection with logic circuitry, a processor, an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

Exemplary system data 1303 is depicted comprises:
a. Raw image data (not pictured) from the polarimeter 1001 (FIG. 1) obtained from step 9001 of the method 900 (FIG. 9).
b. Corrected image data (not pictured), which is the data that has been corrected for non-uniformity, optical distortion, and registration per step 9002 of the method 900 (FIG. 8).
c. IR and Polarization images obtained from step 9003 of the method 900 (FIG. 3).

d. Conversion of polarization and radiance data to multi-dimensional image data applied in step 9004 of the method 900 (FIG. 9).
e. Contrast enhancing algorithms applied to image data in step 9005 of the method 900 (FIG. 9).
f. Image data applied to the display 108 and annunciator 109 in step 9006 of the method 900 (FIG. 9).
g. Radiance image data as described herein.
h. Hybrid radiance/polarization images as described herein.

Figure 9:
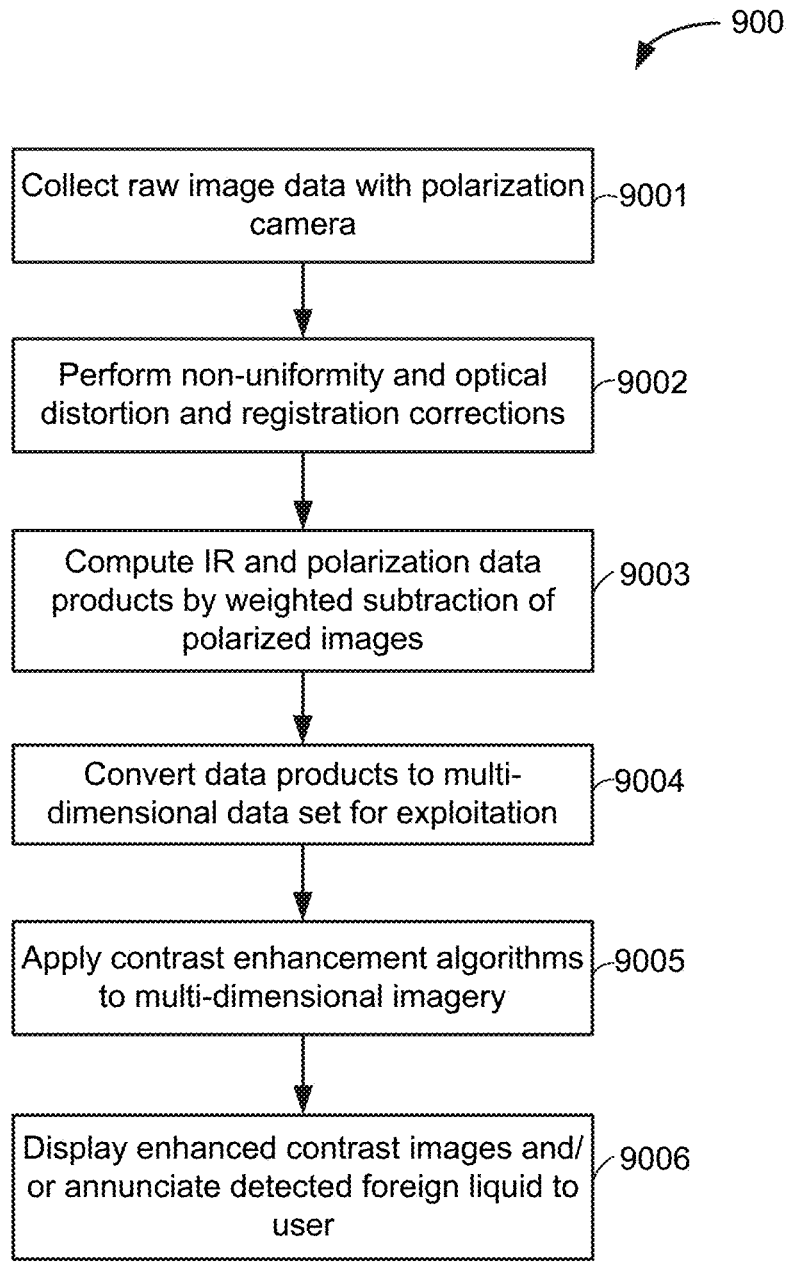
FIG. 9 is a flowchart depicting exemplary architecture and functionality of the image processing logic in accordance with a method according to the present disclosure.

The image processing logic 1302 executes the processes described herein with respect to FIG. 9.

Referring to FIG. 8, an external interface device 1305 connects to and communicates with the display 108 and annunciator 109. The external interface device 1305 may also communicate with or comprise an input device, for example, a keyboard, a switch, a mouse, a touchscreen, and/or other type of interface, which can be used to input data from a user of the system 100. The external interface device 1305 may also or alternatively communicate with or comprise a personal digital assistant (PDA), computer tablet device, laptop, portable or non-portable computer, cellular or mobile phone, or the like. The external interface device 1305 may also or alternatively communicate with or comprise a non-personal computer, e.g., a server, embedded computer, field programmable gate array (FPGA), microprocessor, or the like.

The external interface device 1305 is shown as part of the signal processing unit 1002 in the exemplary embodiment of FIG. 8. In other embodiments, the external interface device 1305 may be outside of the signal processing unit 1002.

The display device 108 may consist of a tv, lcd screen, monitor or any electronic device that conveys image data resulting from the method 900 or is attached to a personal digital assistant (PDA), computer tablet device, laptop, portable or non-portable computer, cellular or mobile phone, or the like. The annunciator device 109 can consist of a warning buzzer, bell, flashing light, or any other auditory or visual or tactile means to warn the operator of the detection of foreign fluids.

In some embodiments, autonomous action may be taken based upon the foreign fluid 102 (FIG. 1) detected. For example, a clean-up response may be automatically initiated. In some cases where automatic action is taken, the annunciator 109 may not be required.

In other embodiments, a Global Positioning System ("GPS") device (not shown) may interface with the external interface device 1305 to provide a position of the foreign fluids 102 detected.

In the illustrated embodiment, the display 108 and annunciator 109 are shown as separate, but the annunciator 109 may be combined with the display 108, and in another embodiments, annunciation could take the form of highlighted boxes or regions, colored regions, or another means used to highlight the object as part of the image data display. See, for example, the red colored region in FIG. 12, which provides a visual indication of a foreign fluid 102 detected.

FIG. 9 is a flowchart depicting exemplary architecture and functionality of the image processing logic 1302 (FIG. 8) in accordance with a method 900. In step 9001 of the method 1000, the polarimeter 1001 captures an image of water 101 and foreign fluid 102 (FIG. 1) and sends raw image data to the signal processing unit 1002 (FIG. 1).

In step 9002, the signal processing unit 1002 (FIG. 1) corrects imager non-uniformity of the images received from the polarimeter 1001. Examples of imager non-uniformity include fixed pattern lines in the image, noisy pixels, bad pixels, bright spots, and the like. Algorithms that are known in the art may be used for correcting the imager non-uniformity. In some embodiments, step 9002 is not performed because the imager non-uniformity does not require correction.

Additionally in step 9002, the signal processing unit 1002 removes image distortion from the image data. An example of image distortion is warping at the edges of the image caused by the objective imaging lens system. Algorithms that are known in the art may be used for correcting image distortion. Registration corrections may also be performed in step 9002, using methods known in the art.

In step 9003, IR and polarization data products are computed. In this step, Stokes parameters ($S_0$, $S_1$, $S_2$) are calculated by weighted subtraction of the polarized image obtained in step 9002. The IR imaging polarimeter measures both a radiance image and a polarization image. A radiance image is a standard image whereby each pixel in the image is a measure of the radiance, typically expressed in Watts/cm2-sr, reflected or emitted from that corresponding pixel area of the scene. Standard photographs and IR images are radiance images, simply mappings of the radiance distribution emitted or reflected from the scene. A polarization image is a mapping of the polarization state distribution across the image. The polarization state distribution is typically expressed in terms of a Stokes image.

Of the Stokes parameters, $S_0$ represents the conventional IR image with no polarization information. $S_1$ and $S_2$ display orthogonal polarimetric information. Thus the Stokes vector, first introduced by G. G. Stokes in 1852, is useful for describing partially polarized light and is defined as $$\vec{S} = \begin{bmatrix} S_0 \\ S_1 \\ S_2 \\ S_3 \end{bmatrix} = \begin{bmatrix} I_0 + I_{90} \\ I_0 - I_{90} \\ I_{45} - I_{135} \\ I_R - I_L \end{bmatrix} \quad (1)$$

Where $I_0$ is the radiance that is linearly polarized in a direction making an angle of 0 degrees with the horizontal plane, $I_{90}$ is radiance linearly polarized in a direction making an angle of 90 degrees with the horizontal plane. Similarly $I_{45}$ and $I_{135}$ are radiance values of linearly polarized light making an angle of 45° and 135° with respect to the horizontal plane. Finally $I_R$ and $I_L$ are radiance values for right and left circularly polarized light. For this invention, right and left circularly polarized light is not necessary and the imaging polarimeter does not need to measure these states of polarization. For this reason, the Stokes vectors that we consider will be limited to the first 3 elements which express linearly polarized light only, $$\vec{S} = \begin{bmatrix} S_0 \\ S_1 \\ S_2 \end{bmatrix} = \begin{bmatrix} I_0 + I_{90} \\ I_0 - I_{90} \\ I_{45} - I_{135} \end{bmatrix} \quad (2)$$

Also in step 9003, a degree of linear polarization (DoLP) image is computed from the Stokes images. A DoLP image is useful for providing contrast for foreign fluids on a water surface, and can be calculated as follows:

$$\text{DoLP} = \sqrt{(s_1/s_0)^2 + (s_2/s_0)^2} \quad (3)$$

In step 9004, the IR and polarization data products and DoLP computed in step 9003 are converted to a multidimensional data set for exploitation. Note that DoLP is linear polarization. As one with skill in the art would know, in some situations polarization that is not linear (e.g., circular) may be desired. Thus in other embodiments, step 9004 may use polarization images derived from any combination of $S_0$, $S_1$, $S_2$, or $S_3$ and is not limited to DoLP.

The DoLP image is one available image used to view polarization contrast in an image. Another alternative image to view polarization content is a "ColorFuse" image that is generated by mapping the radiance, DoLP, and orientation images to a color map. "ColorFuse" is one embodiment of multidimensional representation that can be produced in step 9004. Those knowledgeable in the art can conceive similar mappings. For one example, the DoLP information may be emphasized when radiance values are low.

Persons with skill in the art makes the following mapping of polarization data to a hue-saturation-value representation for color:

$S_0$=value
DoLP=saturation
Orientation ϕ=hue

This representation enables display of all optical information (radiance and polarization) in a single image and provides a means to show both radiometric and polarization contrast enhancing understanding of the scene. In many cases where polarization contrast is strong, this representation provides scene context for the surfaces or objects that are polarized. Those experienced in the art can imagine other ways of doing this.

Because the underlying optical radiation depends on emission, no additional light sources, illumination, or ambient light is required for polarization imaging. Further, the approach works equally well during the night time as it does during the day.

In step 9005, contrast enhancing algorithms that are known in the art are applied to the multidimensional image from step 9004. The multi-dimensional data exploits the polarization data to significantly enhance the information content in a scene. Non-restrictive examples include global mean, variance, and higher order moment analysis, Principal Component Analysis, or Linear Discriminate Analysis, computation of the statistics of the multidimensional data as a whole and then computation of local values based on a kernel convolved with the image as a whole and then normalized by global statistics of the scene.

In step 9006, the contrast enhanced image of the detected oil is displayed to an operator. The detected oil is then annunciated to the user through visual or auditory means. Non-restrictive examples includes bells, buzzers or lights to draw the operator's attention to the display, or indications on the display such as distinctive colors or boxes in the region of the foreign fluid.

In other embodiments, steps 9003, 9004, 9005, and 9006 are used in combinations that omit one or more of the steps. In other embodiments, the polarization image data, or the multi-dimensional (e.g. ColorFuse) data, may be viewed by humans for fluid detection, and no algorithms are applied.

Algorithms that exploit a combination of image features extracted from an IR imaging polarimeter can be used to detect foreign fluids. Once potential noteworthy features are detected, they can be automatically highlighted for the operator, and a warning can be given through some annunciation mechanism (buzzer or light).

Figure 10B:
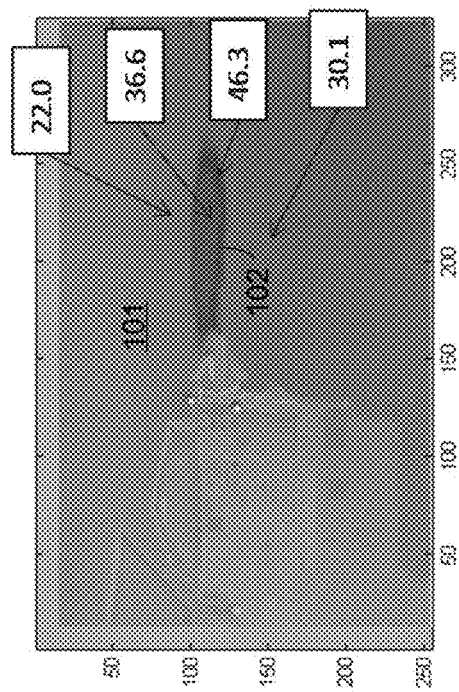
FIG. 10b is a polarization image of the foreign fluid on water at night of FIG. 10a, depicting exemplary improvements of fluid detection of the polarization image
Figure 10A:
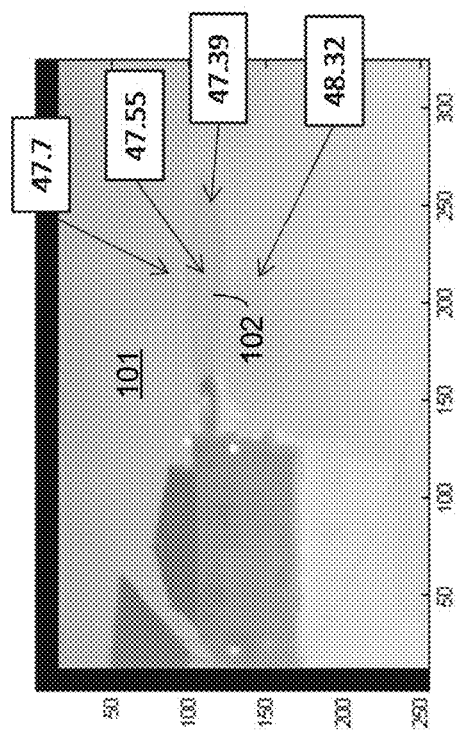
FIG. 10a is a thermal image of a foreign fluid on water at night.

FIGS. 10a and 10b are thermal and polarization images, respectively, of a foreign fluid (e.g., oil) on water at night depicting exemplary improvements of fluid detection of the polarization image. The values on the images show radiometric quantities for the thermal image and polarization quantities for the polarization image at various locations on the surface of the water 101 and in the area of the foreign fluid 102. For the thermal image, the contrast between the fluid and water is very slight. For the polarization image, the contrast is significantly better.

Figure 11B:
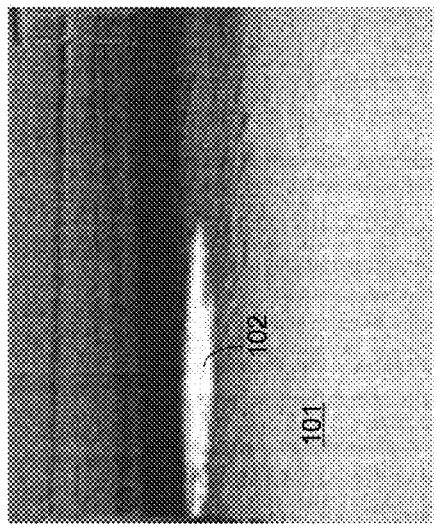
FIG. 11b is an exemplary polarization image of the foreign fluid of FIG. 11a, also at night.
Figure 11D:
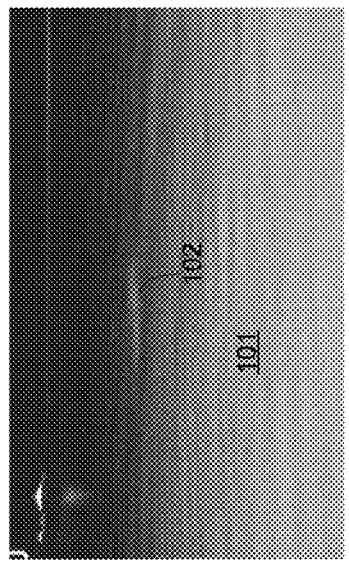
FIG. 11d is an exemplary polarization image of the foreign fluid of FIG. 11e, also at night and with the polarimeter at the same shallow angle as the thermal camera in the image of FIG. 11c.
Figure 11A:
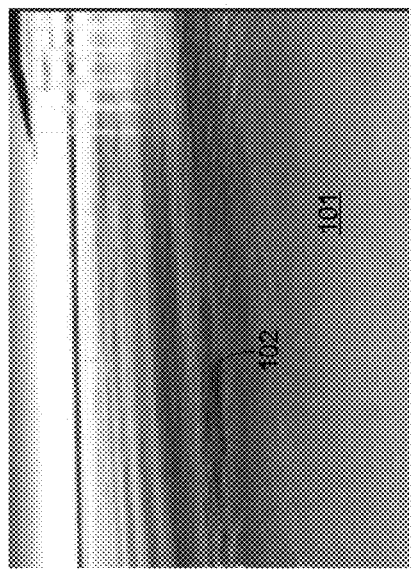
FIG. 11a is an exemplary thermal image of a foreign fluid on water at night.

FIG. 11a is an exemplary thermal image of a foreign fluid 102 on water 101 at night. As can be seen in FIG. 11a, the foreign fluid 102 is barely detectable in the thermal image.

FIG. 11b is an exemplary polarization image of the foreign fluid 102 of FIG. 11a, also at night. Importantly, no external light source is used with the method disclosed herein. The polarization image of FIG. 11b was produced using the method disclosed herein. The foreign fluid 102 is easily detectible in the polarization image. The polarization image of FIG. 11b shows a significant improvement over the thermal image of FIG. 11a. In FIGS. 11a and 11b, the thermal camera and polarimeter, respectively, were positioned at an oblique angle to the water's surface 101.

Figure 11C:
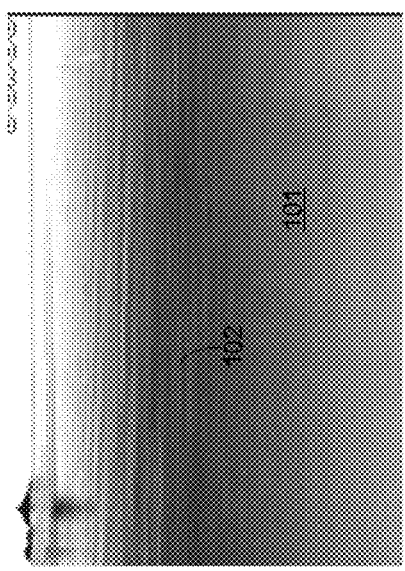

FIG. 11c is an exemplary thermal image of the foreign fluid 102 of FIG. 11a on water 101 at night, with the polarimeter at a shallower angle than the image of FIG. 11a. The images of FIGS. 11a and 11b were taken at roughly 15 degrees and the images of FIGS. 11c and 11d were taken at roughly 5 degrees. As can be seen in FIG. 11c, the foreign fluid 102 is really not detectable in the thermal image.

FIG. 11d is an exemplary polarization image of the foreign fluid 102 of FIG. 11c, also at night and with the polarimeter at the same shallow angle as the thermal camera was in the image of FIG. 11c. The foreign fluid 102 is easily detectible in the polarization image. The foreign fluid 102 is still easily detected in the polarization image of FIG. 11d. In FIGS. 11a and 11b, the thermal camera and polarimeter, respectively, were positioned at an oblique angle to the water's surface 101.

Figure 12B:
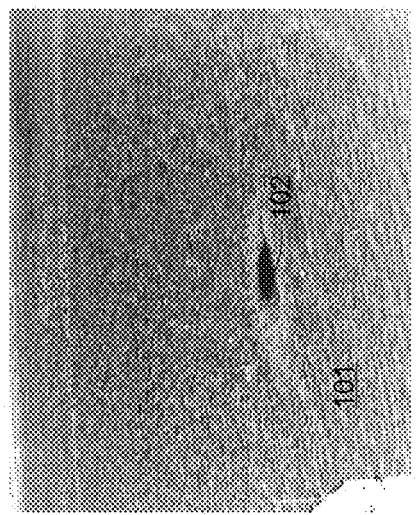
Figure 12C:
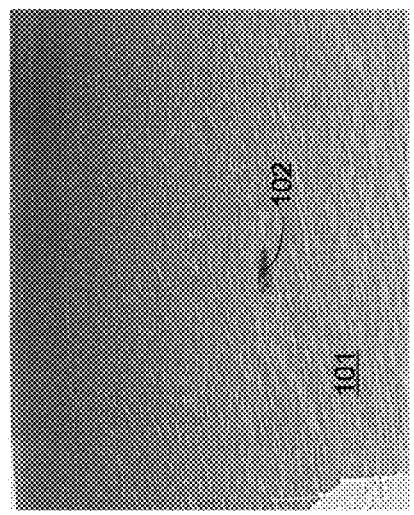
Figure 12A:
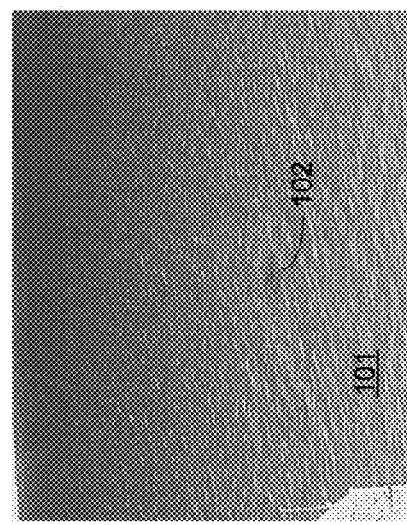
FIG. 12a is a thermal image of a foreign fluid on water.

FIGS. 12a, 12b and 12c are a thermal, polarization, and ColorFuse images, respectively, of a foreign fluid 102 on water 101. The thermal image of FIG. 12a shows very little contrast, the polarization image of FIG. 12b shows strong contrast, and the ColorFuse image of FIG. 12c highlights in red the detection of the foreign fluid.

Figure 13A:
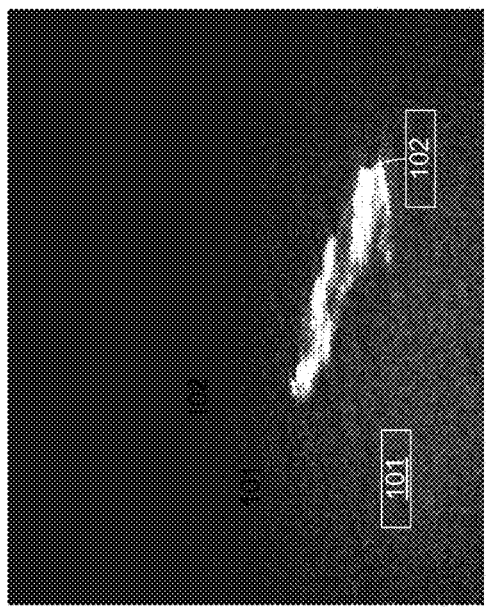
FIG. 13a is a thermal image of the oil spill off the cost of Santa Barbara, Calif. in the summer of 2015, showing oil on the surface of the water.
Figure 13B:
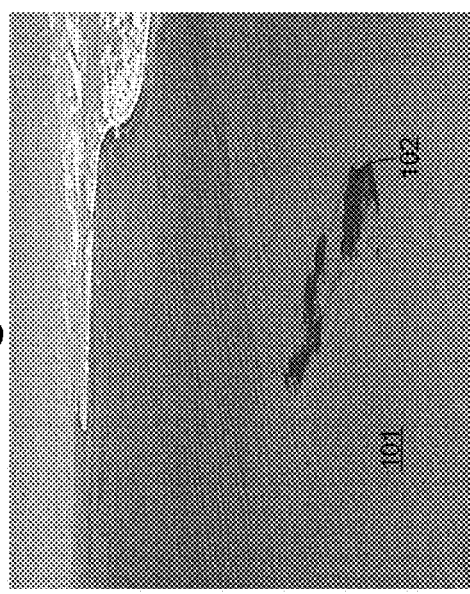
Figure 13C:
FIG. 13c is a polarization image of the same spill showing the oil clearly visible.
Figure 13D:
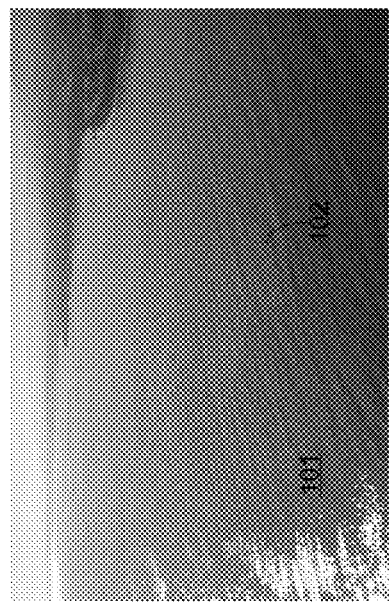
FIG. 13d is a ColorFuse image of the same spill, showing the oil highlighted in red.

FIG. 13a is a thermal image of the oil spill off the cost of Santa Barbara, Calif. in the summer of 2015, showing the oil 102 on the surface of the water 101. FIG. 13b is a visible image of the spill of FIG. 13a. FIG. 13c is a polarization image of the same spill showing the oil 102 clearly visible. FIG. 13d is a ColorFuse image of the same spill, showing the oil 102 highlighted in red.

What is claimed is:

1. A method of detecting a foreign fluid on a surface, the method comprising:
  recording raw image data of the surface using a polarimeter to obtain polarized images, where the recording raw image data using a polarimeter is not dependent on an external light source, including sunlight, and is not dependent on the brightness of available light;
  computing IR and polarization data products from the polarized images;
  converting the IR and polarization data products to a multi-dimensional data set to form multi-dimensional imagery;
  applying contrast enhancement algorithms to multi-dimensional imagery to form enhanced contrast images;
  detecting foreign fluid on the surface from the enhanced contrast images.

2. The method of claim 1, further comprising generating a map of foreign fluid detected.

3. The method of claim 1, further comprising displaying the enhanced contrast images to a user.

4. The method of claim 1, further comprising annunciating detected foreign fluid to a user.

5. The method of claim 1, further comprising performing corrections on the polarized images to correct the polarized images for non-uniformity.

6. The method of claim 5, wherein the step of performing corrections on the polarized images further comprises performing optical distortion and registration corrections.

7. The method of claim 1, wherein the step of computing IR and polarization data products from the polarized images comprises calculating Stokes parameters S0, S1, and S2 from the polarized images to create Stokes images by weighted subtraction of the polarized images.

8. The method of claim 7, further comprising computing polarization images derived from the Stokes images.

9. The method of claim 8, wherein the step of computing polarization images derived from the Stokes images comprise computing a DoLP image from the Stokes images.

10. The method of claim 9, further comprising determining an optimal position of the polarimeter to take images of the surface by determining an optimal range of angles for positioning the polarimeter based upon differences in a DoLP response of the surface and the foreign fluid.

11. The method of claim 9, further comprising mapping the DoLP images and IR images to a color map, wherein the color map shows the detected fluid as a desired color.

12. The method of claim 1, wherein the foreign fluid is oil.

13. A system for detecting a foreign fluid on a surface, the system comprising:

a polarimeter configured to take images of the surface without depending on an external light source, including sunlight, and without depending on the brightness of available light; and a signal processing unit configured to:
 record images taken of the surface from the polarimeter and store the polarized images;
 compute IR and polarization data products from the polarized images;
 convert the IR and polarization data products to a multi-dimensional data set to form multi-dimensional imagery; and
 detect foreign fluid on the surface.

14. A system for detecting a foreign fluid on a surface, the system comprising:

a polarimeter configured to take images of the surface; and a signal processor configured to:
 estimate an expected polarization response for a foreign fluid desired to be detected;
 determine, from the estimated expected polarization response, an optimal position of a polarimeter to take images of the surface;
 position the polarimeter at the optimal position for taking images of the surface;
 record images taken of the surface from the polarimeter and store the polarized images;
 compute IR and polarization data products from the polarized images;
 convert the IR and polarization data products to a multi-dimensional data set to form multi-dimensional imagery; and
 detect foreign fluid on the surface.

* * * * *